(12) United States Patent
Ledig

(10) Patent No.: US 6,511,852 B1
(45) Date of Patent: Jan. 28, 2003

(54) APPARATUS FOR COLLECTING A VOLATILE COMPOSITION OF MATTER RELEASABLY BONDED TO A PLIABLE POROUS SUBSTRATE AND PROCESS FOR USING SAID APPARATUS

(75) Inventor: Walter O. Ledig, Matawan, NJ (US)

(73) Assignee: International Flavors & Fragrances Inc., New York, NY (US)

(*) Notice: Subject to any disclaimer, the term of this patent is extended or adjusted under 35 U.S.C. 154(b) by 0 days.

(21) Appl. No.: 09/336,055

(22) Filed: Jun. 18, 1999

(51) Int. Cl.$^7$ .............................................. G01N 1/22
(52) U.S. Cl. ..................... 436/181; 436/174; 436/176; 436/178; 73/23.34; 73/23.41; 73/23.42; 73/863.23
(58) Field of Search ................... 73/23.34, 23.2, 73/23.41, 23.42, 863.23, 865.7, 866, 863.02; 436/181

(56) References Cited

U.S. PATENT DOCUMENTS

| | | | | |
|---|---|---|---|---|
| 4,003,257 A | * | 1/1977 | Fletcher et al. | 73/19.02 |
| 4,080,182 A | * | 3/1978 | Vitovec et al. | 96/7 |
| 4,249,918 A | | 2/1981 | Argo et al. | |
| 4,462,880 A | * | 7/1984 | Hill et al. | 73/19.1 |
| 4,849,179 A | * | 7/1989 | Reinhardt et al. | 422/89 |
| 5,191,211 A | * | 3/1993 | Gorman | 250/282 |
| 5,242,836 A | | 9/1993 | Ruse | |
| 5,263,359 A | | 11/1993 | Mookherjee et al. | 73/23.34 |
| 5,305,493 A | * | 4/1994 | Prenn | 15/304 |
| 5,313,821 A | * | 5/1994 | Bett et al. | 73/23.34 |
| 5,363,707 A | * | 11/1994 | Augenblick et al. | 73/864.84 |
| 5,891,729 A | | 4/1999 | Behan et al. | 436/2 |
| 5,891,835 A | | 4/1999 | Vlasblom | 510/143 |
| 6,106,786 A | | 8/2000 | Akahosi | |
| 6,164,144 A | * | 12/2000 | Berg | 73/863.21 |

FOREIGN PATENT DOCUMENTS

EP  0 908 174 A2  4/1999

OTHER PUBLICATIONS

Elmore, et al, *J. Agric. Food Chem.*, 1997, vol. 45, pp. 2638–2641 (title: "Comparison of Dynamic Headspace Concentration on Tenax with Solid Phase Microextraction for the Analysis of Aroma Volatiles").

* cited by examiner

*Primary Examiner*—Jill Warden
*Assistant Examiner*—Yelena Gakh
(74) *Attorney, Agent, or Firm*—Arthur L. Liberman

(57) ABSTRACT

Described is apparatus and a process for collecting for subsequent analysis a volatile composition such as a perfume composition located on the surface and/or in the interstices of a planar pliable porous substrate such as a towel section. A planar surface of the substrate which contains the volatile composition is initially juxtaposed adjacent a solid wall (e.g., glass frit) porous to a nonreactive carrier gas such as air, nitrogen or carbon dioxide, and fully and tightly covers the porous section of the wall. The carrier gas is passed through the porous section of the wall and then through the pliable porous substrate section which is adjacent to the wall; after which the carrier gas contains each component of the volatile composition. The composition-carrier gas mixture is then passed through a trapping substance (e.g., TENAX® a polyphenylene oxide) which entraps the molecules of each component of the volatile composition. The thus-collected volatile composition may be subsequently analyzed (e.g., using GLC and NMR techniques) after removing the trapping substance containing the entrapped components from the apparatus.

8 Claims, 10 Drawing Sheets

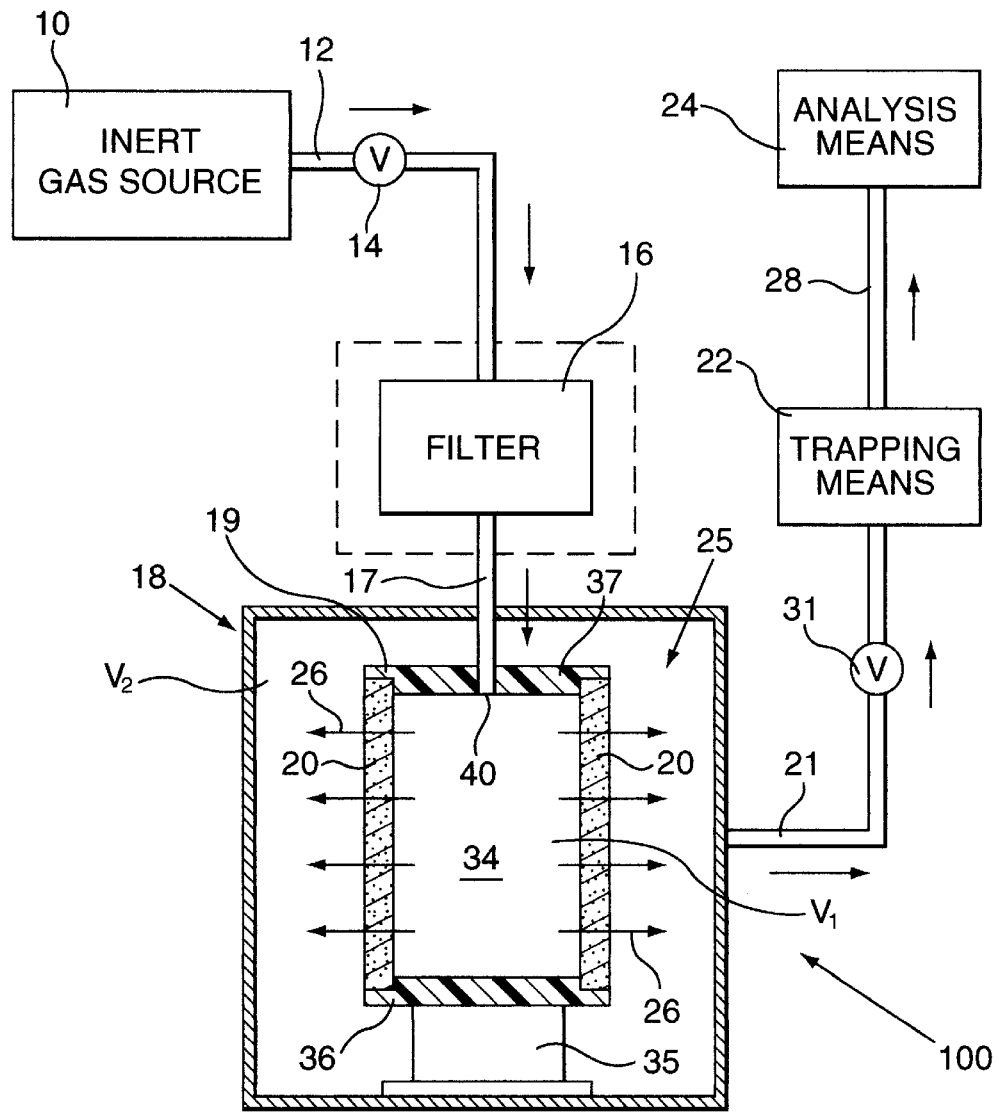
FIG. 1-A

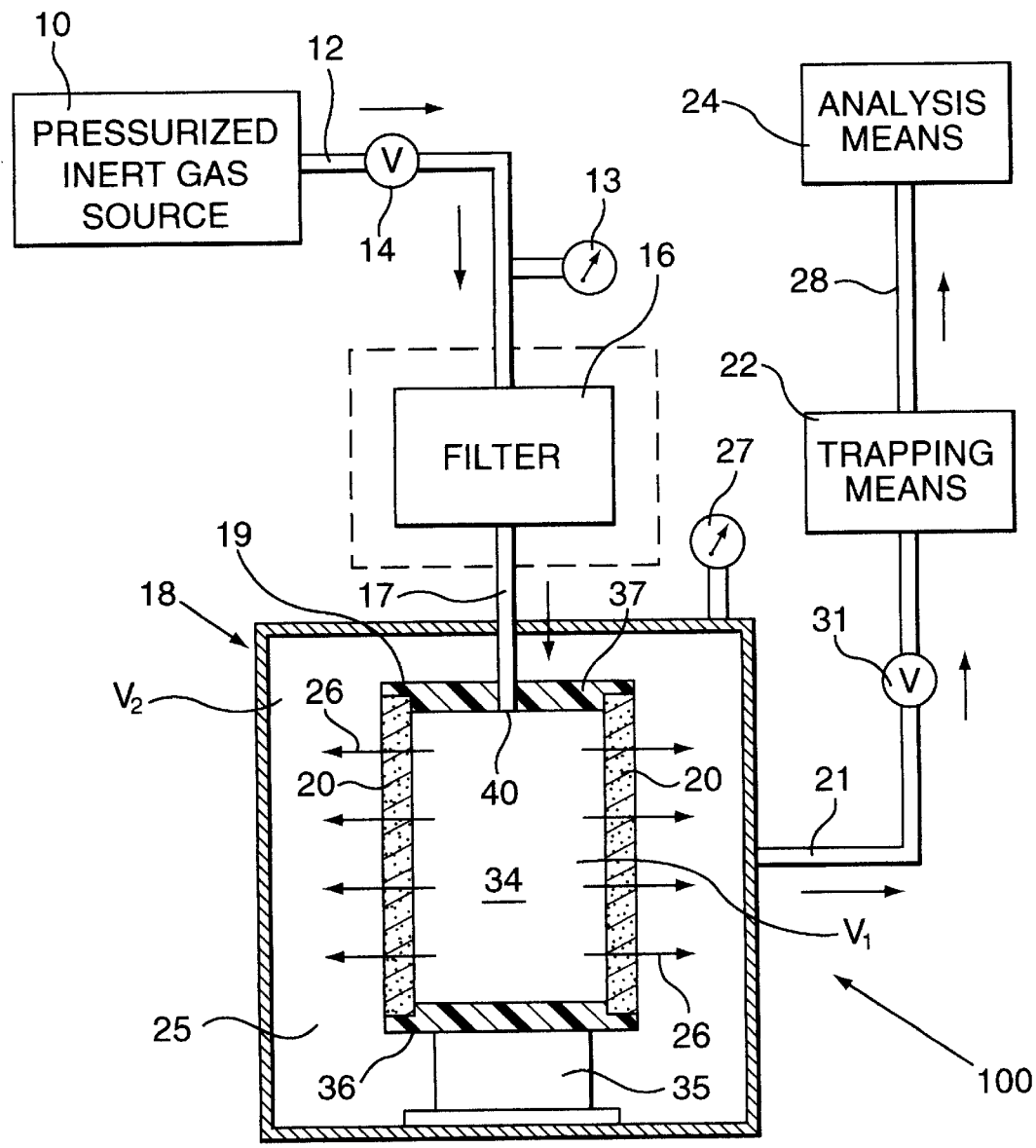
FIG. 1-B

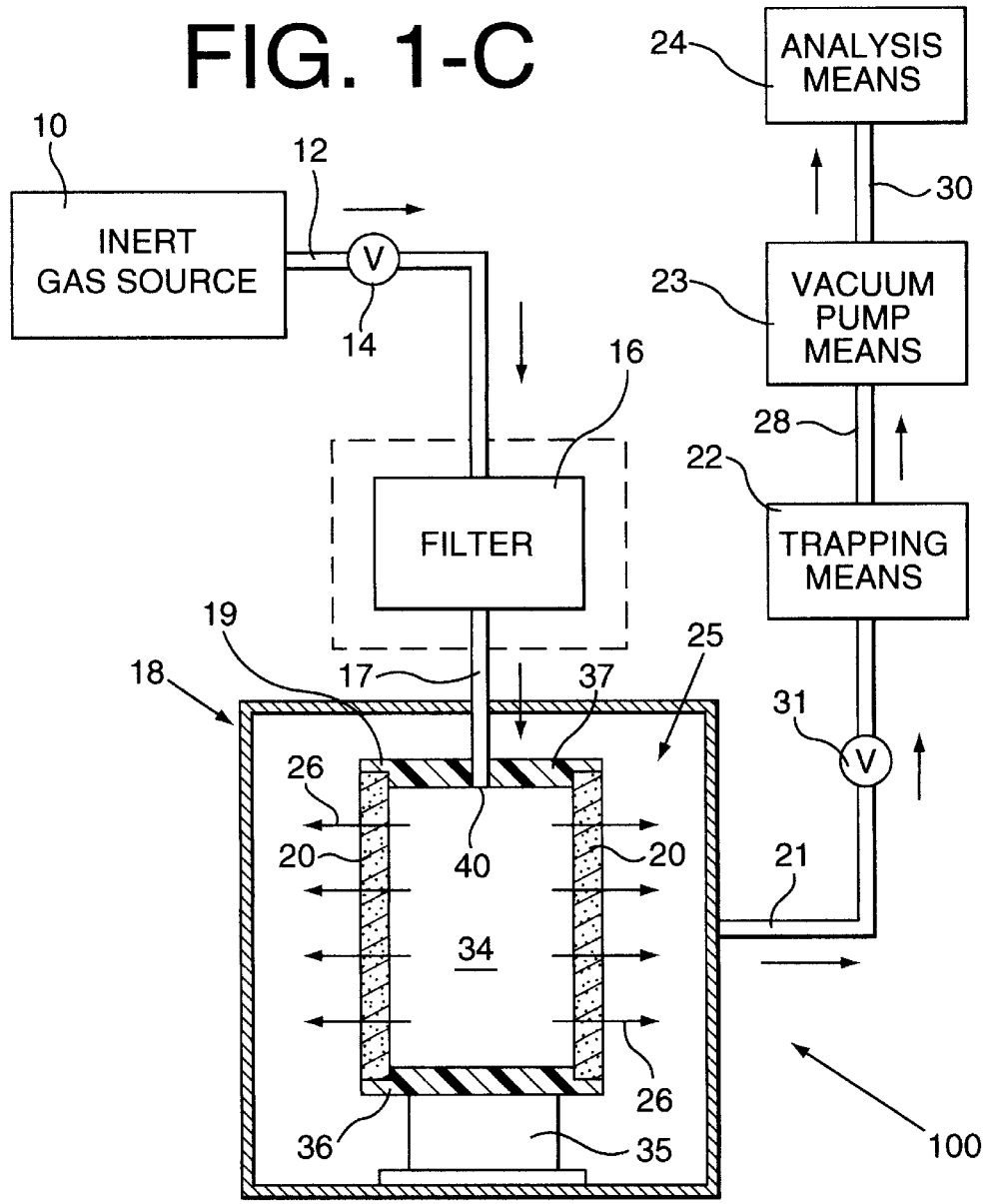

FIG. 1-D
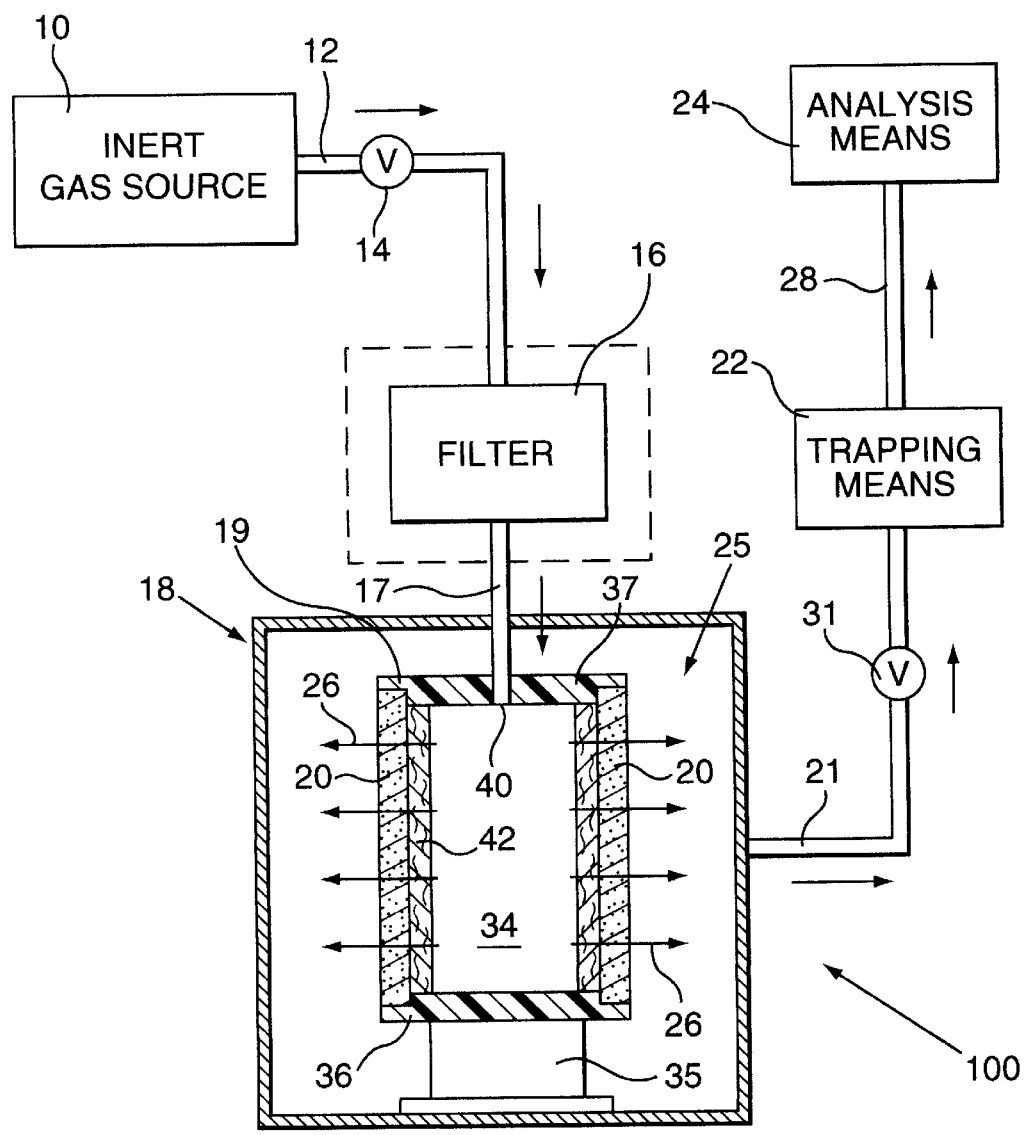

FIG.1-E
PRIOR ART
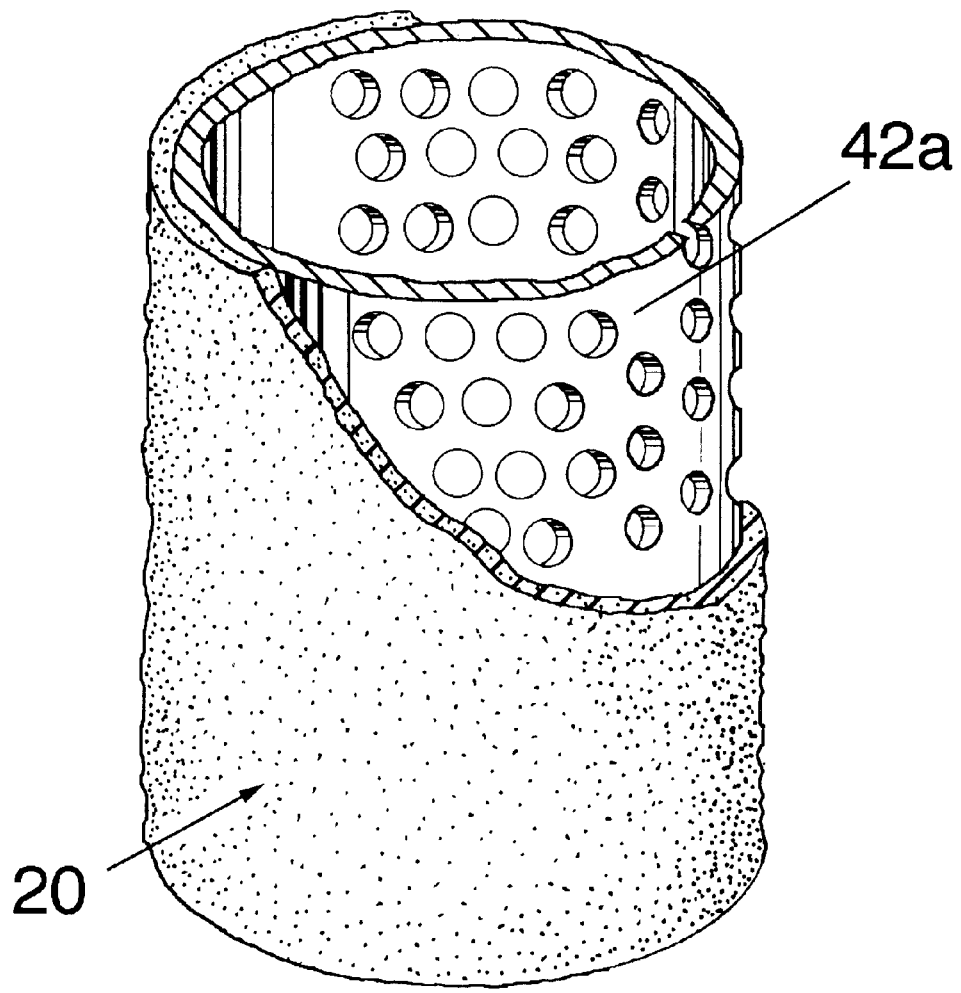

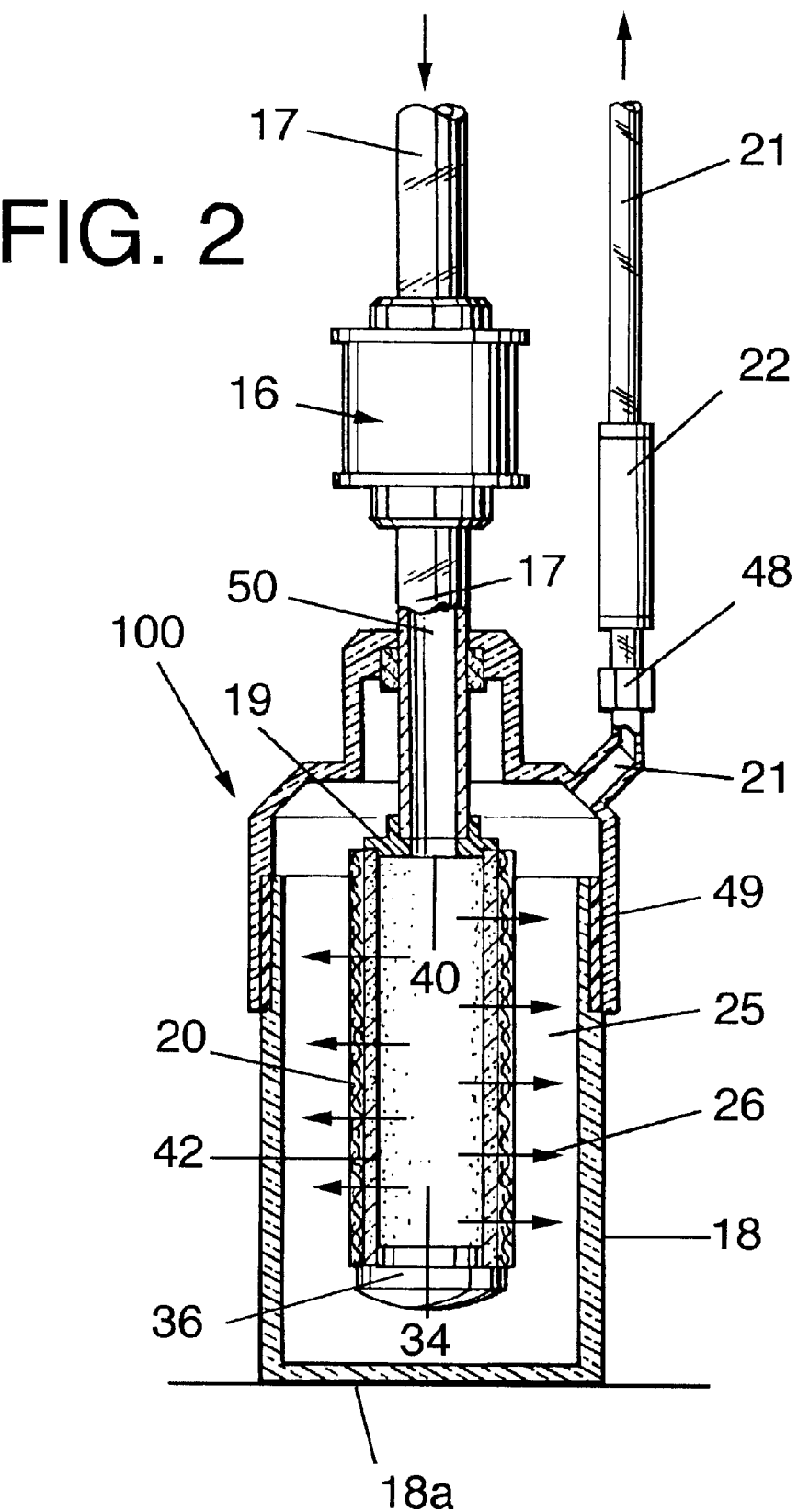

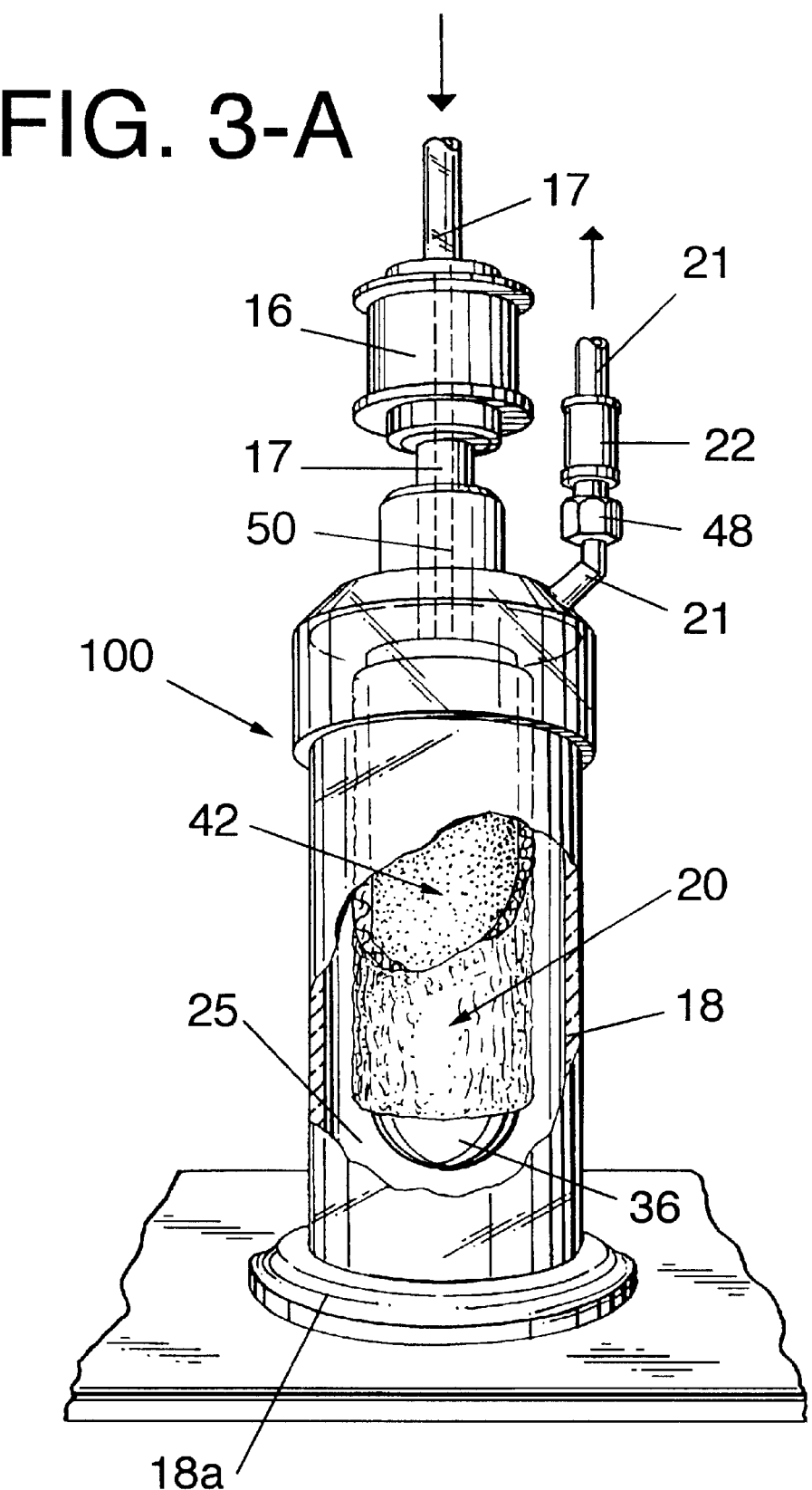

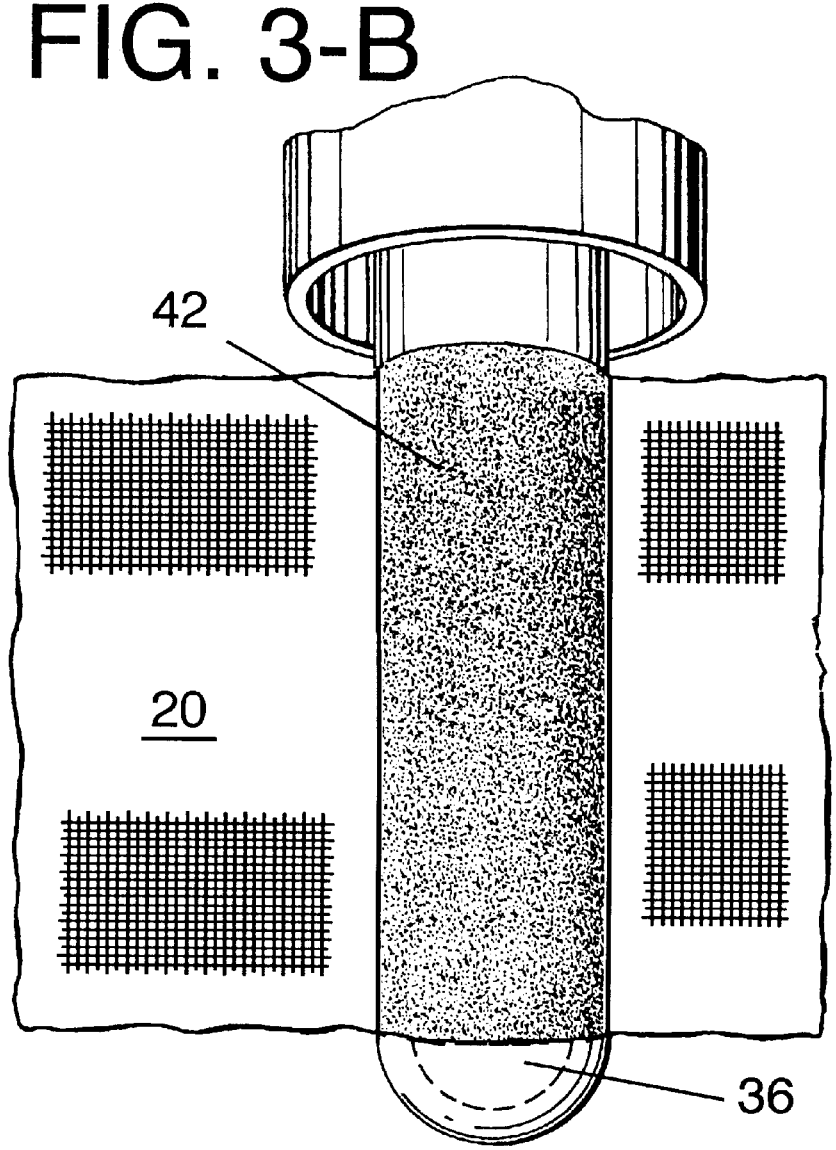
FIG. 3-B

FIG. 3-C
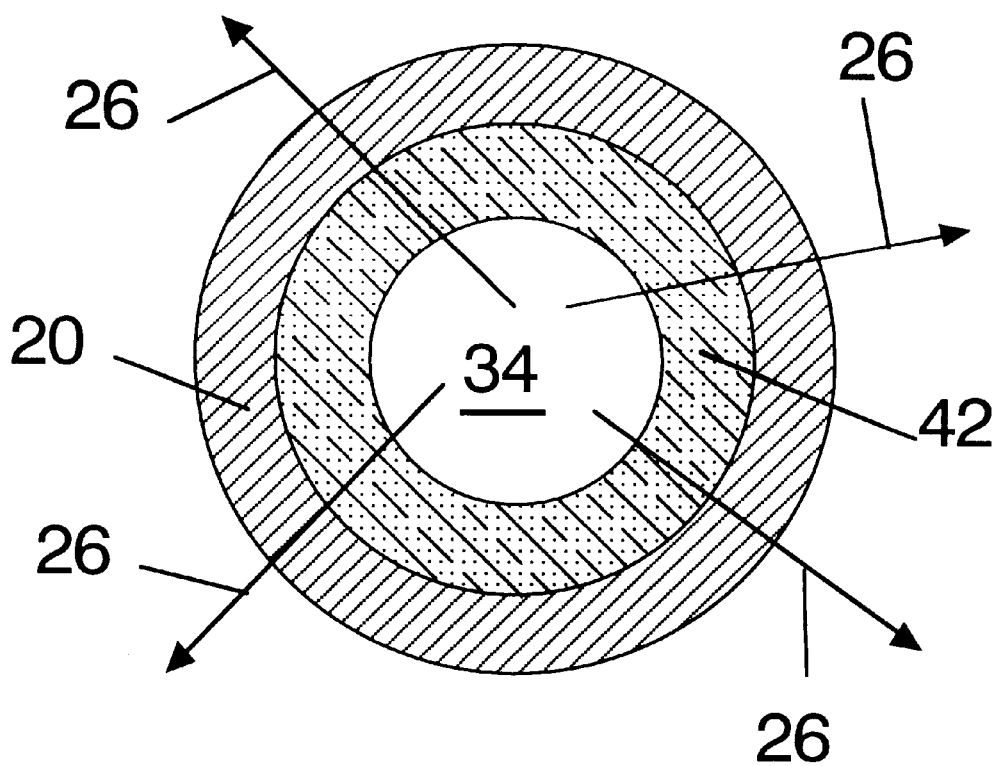

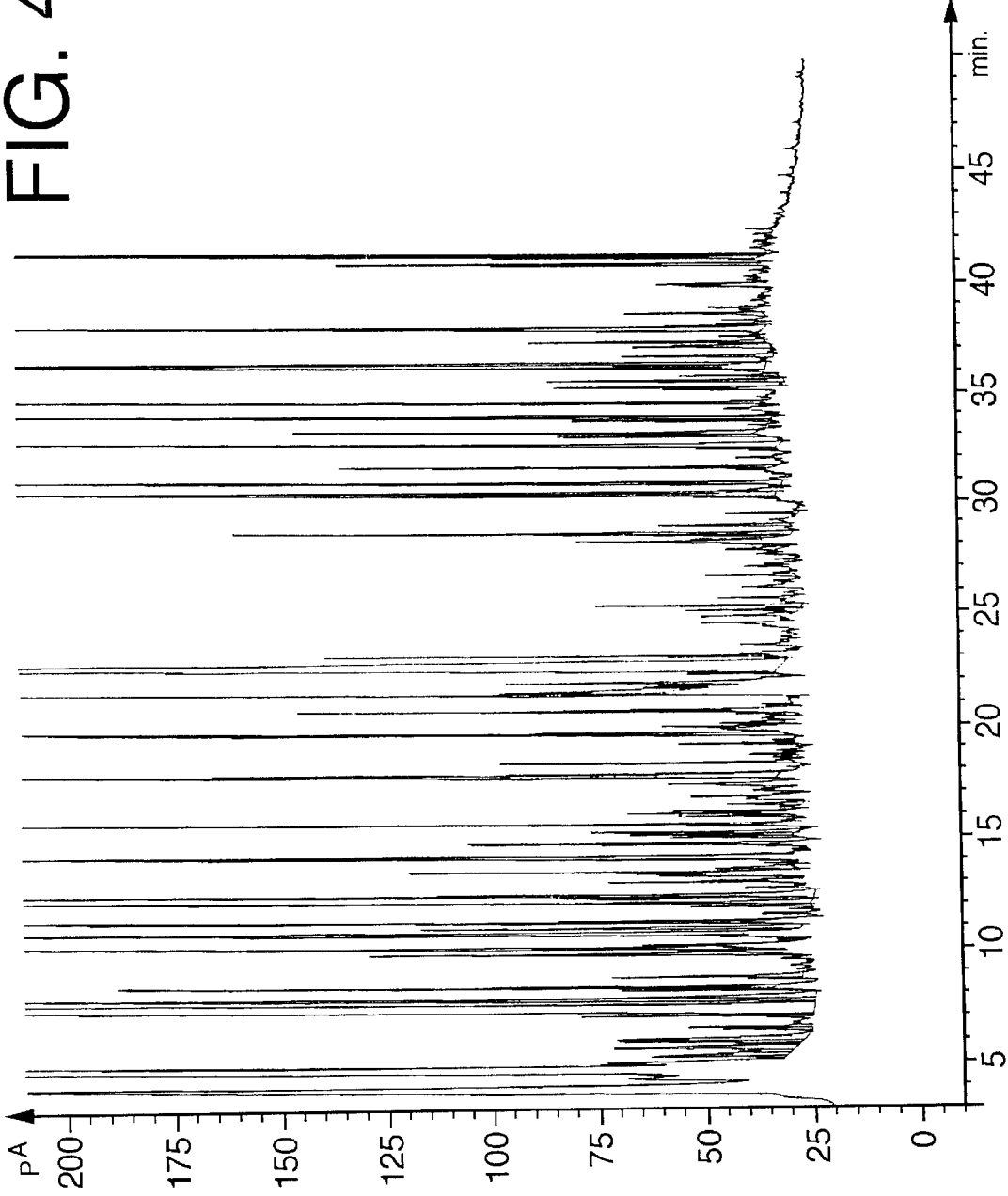

APPARATUS FOR COLLECTING A VOLATILE COMPOSITION OF MATTER RELEASABLY BONDED TO A PLIABLE POROUS SUBSTRATE AND PROCESS FOR USING SAID APPARATUS

BACKGROUND OF THE INVENTION

My invention covers apparatus for collecting (for purposes of subsequent analysis) a volatile composition of matter which is releasably bonded to a pliable porous substrate such as a towel, as well as a process for using such apparatus.

The properties of a pliable substrate (including physical, chemical and microbiological properties) affect the behavior of the substrate with respect to chemicals, particularly volatile chemicals, either naturally present in or on the substrate in a substance applied thereto and so affect the chemicals present in a headspace above the substrate. Conversely, the chemicals entrapped in the interstices of a porous substrate or on the surface of the porous substrate have an effect upon the properties of the substrate, for example, if the substrate is a towel and the towel contains a fragrance, the concentration of that fragrance and the nature of the fragrance in the particular substrate will affect the ultimate aroma in the headspace above the substrate after the substrate is utilized, washed and dried.

Considerably complicated techniques exist in the prior art for collection(for purposes of subsequent analysis) of volatile materials contained within a substrate. U.S. Pat. No. 5,891,729 discloses a method of characterizing a substrate which comprises applying a test formulation to said substrate, subsequently collecting volatile chemicals in a headspace above the substrate, determining a profile of the volatile chemicals so emanated and using said profile to characterize the substrate. Specific examples of substrates in U.S. Pat. No. 5,891,729 are skin, wood, hair, clothing, carpets, plastics, surfaces, ceramic tiles, wool, fabric or perfumed products.

Noting the complexity of the methods and techniques of U.S. Pat. No 5,891,729, it is apparent that a need exists for a more standardized and simplified technique for collection (for purposes of subsequent analysis) of a volatile composition of matter releasably bonded to a pliable porous substrate such as a towel.

Thus, for example, U.S. Pat. No. 5,891,835 issued on Apr. 6, 1999 discloses a cleaner impregnated towel comprising a flexible porous substrate and impregnated into the substrate a cleaner formulation comprising d-limonene, dibasic acid ester, N-methyl-2-pyrrolidone, secondary alcohol ethoxylate, sodium lauryl sulfate, polysorbate 80, a salt of a coconut oil, fatty acid ester of isethionic acid, glycerine, ethyl alcohol, an antimicrobial preservative and, optionally, water. Although the composition impregnated into the substrate is known initially, after the substrate is utilized, there is no teaching of a method for collecting (for purposes of subsequent analysis) the components impregnated into the substrate after initial use or after repeated use of the substrate, nor is there any teaching in U.S. Pat. Nos. 5,891,835 or 5,891,729 of apparatus or processes for a simplified technique for collecting (for purposes of subsequent analysis) the contents of such substrate.

SUMMARY OF THE INVENTION

My invention is directed to apparatus which will effect collection (for purposes of subsequent analysis) of compounds from the headspace over dry cloth as well as moist cloth and other substrates. The compounds are releasably bonded to the surface and/or in the interstices of the porous substrate.

More specifically, my invention is directed to apparatus and a process for collecting for purposes of subsequent analysis a volatile composition such as a perfumery composition located on the surface and/or in the interstices of a planar pliable porous substrate such as a towel section.

In practicing my invention, a planar surface of the substrate which contains the volatile composition is initially juxtaposed adjacent a solid wall (e.g., glass frit) porous to a nonreactive carrier gas such as air, nitrogen or carbon dioxide and fully and tightly covers the porous section of the wall. The carrier gas is passed through the porous section of the wall and then through the pliable porous substrate section which is adjacent the wall, after which the carrier gas will contain each component of the volatile composition. The composition-carrier gas mixture is then passed through a trapping substance (e.g., TENAX® [a polyphenylene oxide]) which entraps the molecules of each component of the volatile composition. The volatile composition can then be analyzed (e.g., using GLC, NMR and mass spectral techniques) after removing the trapping substance containing the entrapped components from the apparatus.

Thus, my invention is directed to apparatus for collecting for purposes of subsequent analysis a volatile substance such as a perfumery material releasably bonded to a substantially planar pliable porous substrate having an inner surface and an outer surface. The substrate is porous to the passage of a carrier gas therethrough in a direction substantially perpendicular to the inner and outer surfaces of the planar pliable porous substrate. The apparatus consists essentially of:

(a) hollow enclosure means (which can be cylindrically shaped or elliptical-cylindrically shaped) consisting of:
 i. hollow outer enclosure means circumventing a first void space and consisting essentially of a base supporting a substantially cylindrical gas impermeable wall having exit port means therethrough;
 ii. entirely surrounded by said hollow outer enclosure means, substantially cylindrically-shaped inner enclosure means situated within said first void space and circumventing a second void space, and having two spaced-apart oppositely situated end sections and a central section juxtaposed to and communicating with each of said oppositely-situated end sections, said central section being substantially parallel to the wall of said outer enclosure means, said central section having an outer surface and an inner surface, and said central section consisting of a cylindrically-shaped gas-permeable hollow frit structure for both (A) supporting the pliable porous substrate whereby, when in use, said porous substrate fully covers said laminar gas-permeable central section in an all-encompassing manner and (B) enabling carrier gas to flow from within said inner enclosure means second void space to the void space located between the outer enclosure means and the inner enclosure means, in a direction substantially perpendicular to and through said porous substrate, each of the two end sections being impervious to the flow of gas therethrough and one of the end sections having an entry port means communicating from without said hollow enclosure means to the second void space within said inner enclosure means;
(b) analyte collection means located downstream from said hollow enclosure means and communicating with the exit port means thereof, consisting essentially of tube trapping means whereby analyte mixture components emitted from said pliable porous substrate during gas flow therethrough are entrapped in said tube trapping means;

(c) upstream from said hollow enclosure means or downstream from said analyte collection means, inert gas flow effecting means for effecting the flow of inert gas sequentially (I) through said entry port means; (II) through the porous pliable substrate means located on said hollow frit structure; (III) through said exit port means; and (IV) through said analyte collection means.

My invention is also directed to a process for collecting (for purposes of subsequent analysis a volatile substance (such as a fragrance composition or an insect-repelling composition) releasably bonded to a substantially planar pliable porous substrate (for example, a cloth or a towel fabricated from cotton or polyester) having an inner surface and an outer surface comprising the steps of:

(a) providing the apparatus as set forth, supra;

(b) providing said porous substrate;

(c) wrapping in an all-encompassing manner said porous substrate around said central section of said inner enclosure means of said apparatus whereby the inner surface of said porous substrate is removably adhered to and intimately adjacent to the entirety of the outer surface of the hollow frit structure of the inner enclosure means;

(d) effecting the flow of carrier gas sequentially (I) from a location upstream from the entry port means; (II) into the inner enclosure means through said entry port means; (III) through said hollow frit structure; (IV) through said porous substrate means in a direction substantially perpendicular thereto in substantially evenly distributed manner across the inner and outer surface thereof; (V) into and through the void space between the inner enclosure means and the outer enclosure means; (VI) through said exit port means of said hollow outer enclosure means; and (VII) into and through said analyte collection means, whereby components of the analyte composition emitted from said porous substrate are trapped in said trapping means.

Preferably, the hollow enclosure means of the above-described apparatus contains two concentric cylindrical enclosures, with the outer cylindrical enclosure being impervious to gas except for an exit port and with the inner enclosure means having an entry port and having a centrally located solid porous surface (e.g., glass frit, or solid microporous polymer).

Preferably, after the pliable porous substrate is in place on the inner enclosure, carrier gas is forced through the inner enclosure past the porous substrate into the outer enclosure and then out of the outer enclosure into the analytical means which preferably contains a trapping material. The carrier gas, such as nitrogen, air or carbon dioxide, is inert and nonreactive with the porous substrate or with the volatile substance releasably bonded to the porous substrate. The carrier gas can either be forced through from a pressurized device upstream from the hollow enclosure means (e.g., a pressurized carbon dioxide cylinder), or the carrier gas can be pulled through using means downstream from the analytical apparatus means such as a vacuum pump.

Whether the inert gas flow effecting means is upstream from the remainder of the apparatus or downstream from the remainder of the apparatus, it is preferable to have a gas filter in place in the apparatus of my invention, upstream from the hollow enclosure means so that the inert gas is free of any contaminants which would interfere with the analysis of the composition releasably bonded to the substantially planar pliable porous substrate (e.g., towel section).

Preferably, the hollow outer enclosure means of the hollow enclosure means part of the apparatus of my invention is cylindrical and has a height dimension of from about 4 cm up to about 20 cm and a diameter dimension of from about 4 cm up to about 12 cm. Preferably, the inner enclosure means of the hollow enclosure means part of the apparatus of my invention is cylindrical and has a height dimension between from about 50% up to about 85% of the height dimension of the hollow outer enclosure means and a diameter dimension of from about 40% up to about 70% of the diameter dimension of the hollow outer enclosure means.

The support means part of the inner enclosure means (that is, the central section of the inner enclosure means) is preferably cylindrical or substantially cylindrical in shape and as stated, supra, is preferably glass frit or microporous polymer. However, other suitable support means are useful in the practice of my invention, for example, the material which is marketed as cylindrical filter screens by the B. C. McDonald & Company of St. Louis, Mo. 63132 under the description of "Ronningen-Petter Woven Wire Screen"; or Ronningen-Petter Woven Synthetic Screen (illustrated in FIG. 1E which is described in the Brief Description of the Drawings and in the Detailed Description of the Drawings sections, infra); or the Ronningen-Petter Perforated Screen. The Ronningen-Petter Screens are manufactured by the Dover Corporation/Ronningen-Petter Division, P.O. Box 188, Portage, Mich. 49081. The Ronningen-Petter Cylindrical Screens useful as support means in the practice of our invention are specifically described in literature published by Ronningen-Petter entitled "how to select filter screens for the removal of trace contaminants in a closed liquid system."

Other support means useful in fabrication of the central section of the inner enclosure means of the apparatus of my invention are described in U.S. Pat. No. 5,762,797 issued on Jun. 9, 1998 entitled "ANTIMICROBIAL FILTER CARTRIDGE," the specification for which is incorporated by reference herein, and U.S. Pat. No. 5,868,933 issued on Feb. 9, 1999 entitled "ANTIMICROBIAL FILTER CARTRIDGE", the specification for which is incorporated by reference herein.

With respect to the analyte collection means located downstream from the hollow enclosure means and communicating with the exit port means of the hollow outer enclosure means, the analyte collection means part of the apparatus of my invention as stated, supra, consists essentially of tube trapping means whereby volatile substance components emitted from the pliable porous substrate during gas flow therethrough are entrapped in the tube trapping means. The tube trapping means preferably consists of a tube having a length in the range of from about 2 cm up to about 4 cm and a diameter of from about 0.1 cm up to about 0.4 cm. Thus, various trapping materials are useful in the practice of my invention. As stated, supra, TENAX® (a polyphenylene oxide, as described infra)is a preferable material. Various forms of TENAX® are useful, for example, TENAX®-GC. TENAX® is a registered trademark of ENKA, N.V. of the Kingdom of the Netherlands (CAS Registration No. 2438-68-9). Other forms of TENAX® and methods of production of such forms of TENAX® are described in the following U.S. Letters Patents, the disclosures of which are incorporated by reference herein:

U.S. Pat. No. 3,400,100 issued on Sep. 30, 1968 ("PROCESS FOR THE PREPARATION OF POLYPHENYLENE ETHERS");

U.S. Pat. No. 3,644,227 issued on Feb. 22, 1972 ("SEPARATION OF POLY(2-6-DIMETHYL-1,4-PHENYLEOXIDE") FROM ITS BLENDS WITH OTHER POLYMERS);

U.S. Pat. No. 3,703,564 issued on Nov. 21, 1972 (BIS-POLYPHENYLENEOXIDE]ESTER BLOCK COPOLYMERS");

U.S. Pat. No. 4,431,779 issued on Feb. 14, 1984 (POLYETHERAMIDE-POLYPHENYLENE ETHER BLENDS"); and U.S. Pat. No. 4801,645 issued on Jan. 31, 1989 ("THERMOPLASTIC RESIN COMPOSITION").

TENAX®-GC is actually a polyphenyleneoxide defined according to the structure:

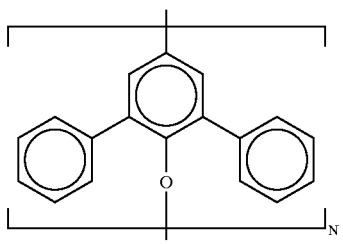

wherein N is an integer of from about 100 up to about 150.

Other trapping materials useful in the practice of my invention are as follows:

Activated Carbon marketed by Aldrich Chemical Company of 1001 West Saint Paul Avenue, Milwaukee, Wis. 53233 (Catalog Nos. 16, 155-1; 29, 259-1; 24, 223-3; 24, 224-1; and 24, 227-6);

Activated Alumina marketed by Sigma Chemical Company of St. Louis, Mo. (Catalog Nos. A8753; A8878; A9003; A1522and A2272);

Silica Gels marketed by Sigma Chemical Company (for example, Catalog Nos. S4004; S6628; and H8506); and CHROMOSORB® (registered trademark of the Johns-Manville Company of Manville, N.J.), such as CHROMOSORB® LC-2; CHROMOSORB® LC-3; AND CHROMOSORB® LC-7, marketed by Sigma Chemical Company under Catalog Nos. C 0641; C 0766; C 5517 and C 6269.

The analyte collection means useful in the practice of my invention may contain, in place of the TENAX® (polyphenylene oxide) trapping substance, solid phase microextraction materials ("SPME" materials) such as those described in Bulletin 869 published by SUPELCO, INC., Supelco Park, Bellefonte, Pa. 16823-0048. An SPME example useful in the practice of my invention is 100 $\mu$m polydimethylsiloxane fiber, Catalog No. 5-7300 of Supelco, Inc. The Supelco, Inc. Bulletin 869 is incorporated by reference herein. An additional description of the SPME (solid phase microextraction) technique useful in conjunction with the practice of my invention is the paper, Elmore, et al, *J. Agric. Food Chem.*, 1997, Volume 45, pages 2638–2641, entitled "Comparison of Dynamic Headspace Concentration or Tenax [TENAX®] with Solid Phase Microextractlon for the Analysis of Aroma Volatiles," incorporated by reference herein.

As stated, supra, the means for effecting the flow of inert gas sequentially (i) through the entry port means of the inner enclosure means; (ii) and through the porous pliable substrate means located on the support means of the apparatus of my invention can be located downstream from the analytical apparatus means. If that is the case, the inert gas flow effecting means is a negative pressure pump means, preferably a vacuum pump of the "low flow" variety, for example, "Low Flow" pumps marketed by the Ametek Company of Largo, Fla. 34643 (the "Ametek Constant flow Sampler").

The flow rate of inert carrier gas past the porous pliable substrate is preferably at a rate in the range of from about 20 ml per minute up to about 200 ml per minute of carrier gas, e.g., nitrogen, air or carbon dioxide.

At the indicated rates of carrier gas flow, a range of molar rates of release of volatile composition will occur from the porous substrate, e.g., towel section, in accordance with the following algorithm:

$$\Delta n = n_1 \left[ \frac{V_1}{V_2} e^{-\frac{2C_V}{zR} \left[ \frac{T_2 - T_1}{T_2 + T_1} \right]} - 1 \right]$$

wherein $n_1$ is the carrier gas flow rate in gram moles per hour;

$\Delta n$ is the molar flow rate in gram moles per hour) of release of volatile composition from the pliable porous substrate;

$V_1$ is the volume of the inner enclosure;

$T_1$ is the temperature of the void space of the inner enclosure in °K (degrees Kelvin);

$V_2$ is the volume between the porous pliable substrate and the outer enclosure;

$T_2$ is the temperature of the carrier gas and volatile composition released from the pliable porous substrate (that is, the temperature of volume $V_2$) in °K;

$$R \text{ is the gas constant} \left[ 0.08206 \frac{\text{liter} - \text{atm}}{\text{gm mole} - °K} \right];$$

z is the compressibility factor of the carrier gas; and $C_v$ is the heat capacity of the carrier gas defined as $$\left( \frac{\partial E}{\partial T} \right)_V,$$

wherein

E is the internal energy of the carrier gas during flow through the apparatus of my invention.

BRIEF DESCRIPTION OF THE DRAWINGS

FIG. 1A is a schematic block flow diagram showing the operation of the apparatus of my invention and the process of my invention.

FIG. 1B is another schematic block flow diagram showing the operation of the apparatus of my invention as well as the process of my invention and showing the use of pressure measuring devices in conjunction with the apparatus of my invention; and, in addition, showing the use of inert gas flow effecting means for effecting the flow of inert gas through the apparatus of my invention, upstream from the hollow enclosure portion of the apparatus of my invention, specifically as a pressurized gas source (e.g., cylinder of pressurized air).

FIG. 1C is another schematic block flow diagram showing the operation of the apparatus of my invention and the process of my invention and also showing inert gas flow effecting means for effecting the flow of inert gas through the apparatus of my invention, which flow effecting means is in the form of vacuum pump means downstream from the analytical apparatus means.

FIG. 1D is another schematic block flow diagram showing the use of the apparatus of my invention when in actual operation analyzing a pliable porous substrate material containing material to be collected(e.g. a fragrance composition)(for purposes of subsequent analysis).

FIG. 1E is a cutaway perspective diagram of an example of a laminar gas-permeable section of the central section of the inner enclosure means of the apparatus of my invention ("Ronningen-Petter Woven Synthetic Screen" manufactured by the Ronningen-Petter Division of the Dover Corporation, P.O. Box 188, Portage, Mich. 49081).

FIG. 2 is a detailed cutaway side elevation view of a preferred embodiment of the apparatus of my invention showing the employment of fritted glass as a laminar gas permeable section of the central section of the inner enclosure means of the apparatus of my invention.

FIG. 3A is a perspective view of a preferred embodiment of the apparatus of my invention, showing the outer enclosure means fabricated from ceramic quartz glass and showing the central part of the inner enclosure means fabricated from fritted glass.

FIG. 3B is a perspective view of a preferred embodiment of that part of the apparatus of my invention which is the inner enclosure means wherein the central section consists of a fritted glass laminar gas-permeable section and wherein the porous pliable planar substrate to be analyzed is a towel section about to be placed fully covering and adjacent to the fritted glass section of the inner enclosure means.

FIG. 3C is a top cutaway schematic view of the inner enclosure means of the apparatus of my invention having juxtaposed and adjacent thereto the porous pliable substrate to be analyzed for a volatile composition contained thereon or in the interstices thereof.

FIG. 4 is the GC-mass spectrum of a fragrance composition releasably bonded to a towel section, which composition was collected (for purposes of subsequent analysis) using the apparatus and process of my invention according to the procedure of Example I, infra (conditions: 50 meter× 320 $\mu$×0.52 $\mu$ bonded fused silica methyl silicone column programmed from 80–220° C. At 8° C. Per minute).

DETAILED DESCRIPTION OF THE DRAWINGS

Referring to FIGS. 1A, 1B, 1C and 1D, gas from gas source 10 is passed through line 12 past valve 14 through carrier gas filter 16 (optionally) through line 17 into the inner enclosure means 19, which is a support means for porous material 20. The carrier gas passes through entry port 40 into void 34. The inner enclosure means has top 37 and base 36. The Inner enclosure means is supported via support 35 within the outer enclosure means 18. Carrier gas flows from void 34 into void 25 of the outer enclosure means (with the flow being shown by reference numeral 26). The carrier gas is then passed through line 21 past valve 31 into and through trapping means 22 wherein components of volatile material from the porous material at 20 are trapped. The trapping substance containing trapped components may then be conveyed via route 28 to analysis means 24 (e.g., NMR, IR and mass spectral analytical equipment) [not part of my invention]. Overall, the apparatus is indicated by reference numeral 100.

Specifically referring to FIG. 1B, pressurized gas (e.g., air) from, for example, a pressurized air vessel 11, is passed through line 12 into the apparatus of my invention, initially through line 17 via entry port 40. In FIG 1B, pressure indicator 13 is located on line 12, and pressure Indicator 27 is located in the outer enclosure means 18 whereby a pressure drop between line 14 primarily across porous wall 20 is measured.

Referring specifically to FIG. 1C, carrier gas from gas source 10 is pulled through the apparatus by means of vacuum pump means 23 located downstream from the trapping means 22. Inert carrier gas is pulled through the apparatus using vacuum pump means 23 through line 28 which is connected to trapping means 22. The resulting trapped components may then be conveyed [on the trapping substance via conveying means 30] to analysis means 24 [not part of my invention].

Referring specifically to FIG. 1D, the central section of inner enclosure means 19 is composed of glass frit shown by reference numeral 42. Carrier gas entering at entry port 40 into void 34 within the inner enclosure means then passes through the glass frit 42 and through the pliable porous substrate 20. The passage of the inert gas again is shown by reference numeral 26 wherein the carrier gas now containing molecules of volatile substance is passed into void 25 of outer enclosure means 18.

Referring to FIG. 1E, inner support means 42a (Ronningen-Petter Woven Synthetic Screen) supports the pliable porous substrate containing volatile composition therein and/or thereon 20.

Referring to FIG. 2, inert carrier gas, e.g., air, passes through tube 17 past apparatus entry location 50 through entry port 40 (the entry port for the inner enclosure means) into void 34 and then through fritted glass 42 into the void between the outer container means 18 and the inner container means 19. The flow of carrier gas is shown by reference numeral 26. The top of the outer enclosure means is sealed to the lower section thereof 18 (which has base 18a) with Teflon seal 49. The carrier gas containing molecules of volatile substance is then passed through line 21 past Swageloc connector 48 into TENAX® (polyphenylene oxide)trap 22. The fritted glass support 42, in the case of the apparatus of FIG. 2, is 4" in length×1.5" in diameter and will hold a piece of cloth 4" in length×5.25" in width.

Referring to FIG. 3A, the apparatus 100 contains the upper inlet tube 18 and an inner enclosure means 42 having base 36 and outer enclosure means 18 having base 18a. Carrier gas flows through tube 21 into TENAX® (polyphenylene oxide)trap or SPME trap 22.

Referring to FIG. 3B, the pliable porous substrate 20 is a section of a towel which is to be juxtaposed immediately adjacent to and fully covering the fritted glass central part of the inner enclosure means 42.

Referring to FIG. 3C, the void space of the inner enclosure means 34 has carrier gas flowing therethrough in a direction perpendicular to the support means 42 for the pliable porous substrate 20 containing volatile composition (e.g., perfume composition) to be analyzed with the carrier gas flow being shown by reference numeral 26.

The detailed description of the operation of the apparatus of FIG. 3A is set forth in the description of Example I, infra.

Thus, the following Example I is illustrative of my invention, but my invention is only limited by the scope of the claims following said example.

EXAMPLE I

Analysis of Contents of Fragrance Composition Releasably Adhered to Towel

Objective

To analyze the contents of a fragrance material originally situated in the interstices of a cotton towel.

Procedure

A 4"×5.25" cotton towel section containing 0.005% by weight fragrance composition is tightly wrapped around the central section of the inner enclosure of the apparatus of FIG. 3A. The inner enclosure thereof is composed of a porous fritted glass. Air from location 11 (FIG. 1B) is passed through the apparatus at a rate of 40 ml per minute for a period of 7 hours. Trapping means 22 contains a TENAX®-GC(a polyphenylene oxide as described supra) trap. At the end of the 7-hour period, the air flow was terminated and the TENAX®-GC trap was opened and the contents analyzed. The contents of the trap were analyzed by GC-MS analysis using a 50 m×0.32 mm OV-2 fused silica column having conditions: 80–220° C. at 8° C. per minute.

FIG. 4 is the GC mass spectrum for the perfume composition located on the towel, which is the subject of this example.

What is claimed is:

1. A process for carrying out a collection of components of an analyte mixture, for the purpose of effecting the qualitative and quantitative analysis of a volatile analyte composition releasably bonded to a substantially planar pliable porous substrate having an inner surface and an outer surface, said substrate being porous to the passage of a carrier gas therethrough in a direction substantially perpendicular to the inner and outer surfaces of said planar porous substrate, consisting essentially of the steps of:

i. providing an apparatus consisting essentially of:

(a) hollow enclosure means consisting of hollow outer enclosure means circumventing a first void space and consisting essentially of a base supporting a substantially cylindrical gas impermeable wall having exit port means therethrough; and entirely surrounded by said hollow outer enclosure means, substantially cylindrically-shaped inner enclosure means situated within said first void space and circumventing a second void space, and having two spaced-apart oppositely-situated end sections and a central section juxtaposed to and communicating with each of said oppositely-situated end sections, said central section being substantially parallel to the wall of said outer enclosure means, said central section having an outer surface and an inner surface, and said central section consisting of a cylindrically-shaped gas-permeable hollow frit structure for both (A) supporting the pliable porous substrate whereby, when in use, said porous substrate fully covers said laminar gas-permeable central section in an all-encompassing manner and (B) enabling carrier gas to flow from within said inner enclosure means second void space to the void space located between the outer enclosure means and the inner enclosure means, in a direction substantially perpendicular to and through said porous substrate, each of the two end sections being impervious to the flow of gas therethrough and one of said end sections having an entry port means communicating from without said hollow enclosure means to the second void space within said inner enclosure means;

(b) analyte collection means located downstream from said hollow enclosure means and communicating with the exit port means thereof, consisting essentially of tube trapping means whereby analyte mixture components emitted from said pliable porous substrate during gas flow therethrough are entrapped in said tube trapping means;

(c) upstream from said hollow enclosure means or downstream from said analyte collection means, inert gas flow effecting means for effecting the flow of inert gas sequentially (I) through said entry port means; (II) through the porous pliable substrate means located on said hollow frit structure; (III) through said exit port means; and (IV) through said analyte collection means;

ii. providing said porous substrate;

iii. wrapping in an all-encompassing manner said porous substrate around said central section of said inner enclosure means of said apparatus whereby the inner surface of said porous substrate is removably adhered to and intimately adjacent to the entirety of the outer surface of the hollow frit structure of the inner enclosure means; and iv. effecting the flow of carrier gas sequentially (I) from a location upstream from the entry port means; (II) into the inner enclosure means through said entry port means; (III) through said hollow frit structure; (IV) through said porous substrate means in a direction substantially perpendicular thereto in a substantially evenly distributed manner across the inner and outer surface thereof; (V) into and through the void space between the inner enclosure means and the outer enclosure means;

(VI) through said exit port means of said hollow outer enclosure means; and (VII) into and through said analyte collection means, whereby components of the analyte composition emitted from said porous substrate are trapped in said tube trapping means.

2. The process of claim 1 wherein the central section of the inner enclosure means consists of porous glass frit.

3. The process of claim 1 wherein carrier gas filtering means is located immediately upstream from said entry port of said inner enclosure means.

4. The process of claim 1 wherein carrier gas flow is effected by means of positive pressure from a source upstream from said inner enclosure means.

5. The process of claim 1 wherein carrier gas flow is effected into the inner enclosure means by means of negative pressure means downstream from said trapping means.

6. The process of claim 1 wherein the analyte collection means consists of the solid phase microextraction means which is a polydimethylsiloxane fiber.

7. The process of claim 1 wherein the pliable porous substrate is a cotton towel having a fragrance composition located thereon.

8. The process of claim 7 wherein the carrier gas used is air.

* * * * *